United States Patent
He et al.

(10) Patent No.: US 10,300,301 B2
(45) Date of Patent: May 28, 2019

(54) RESPIRATORY GUIDANCE DEVICE AND METHOD APPLIED IN RESPIRATORY-GATED ION BEAM IRRADIATION

(71) Applicant: INSTITUTE OF MODERN PHYSICS, CHINESE ACADEMY OF SCIENCES, Gansu (CN)

(72) Inventors: Pengbo He, Lanzhou (CN); Qiang Li, Lanzhou (CN); Zhongying Dai, Lanzhou (CN); Xinguo Liu, Lanzhou (CN); Ting Zhao, Lanzhou (CN); Tingyan Fu, Lanzhou (CN); Guosheng Shen, Lanzhou (CN); Yuanyuan Ma, Lanzhou (CN); Qiyan Huang, Lanzhou (CN); Yuanlin Yan, Lanzhou (CN)

(73) Assignee: INSTITUTE OF MODERN PHYSICS, CHINESE ACADEMY OF SCIENCES, Lanzhou (CN)

( * ) Notice: Subject to any disclaimer, the term of this patent is extended or adjusted under 35 U.S.C. 154(b) by 209 days.

(21) Appl. No.: 15/315,717

(22) PCT Filed: Sep. 14, 2015

(86) PCT No.: PCT/CN2015/089550
§ 371 (c)(1),
(2) Date: Dec. 1, 2016

(87) PCT Pub. No.: WO2016/045517
PCT Pub. Date: Mar. 31, 2016

(65) Prior Publication Data
US 2017/0106209 A1 Apr. 20, 2017

(30) Foreign Application Priority Data
Sep. 25, 2014 (CN) .......................... 2014 1 0498032

(51) Int. Cl.
A61N 5/10 (2006.01)
(52) U.S. Cl.
CPC ......... *A61N 5/1037* (2013.01); *A61N 5/1048* (2013.01); *A61N 5/1068* (2013.01);
(Continued)
(58) Field of Classification Search
CPC .. A61N 5/1037; A61N 5/1048; A61N 5/1068; A61N 2005/1074; A61N 2005/1087
(Continued)

(56) References Cited

U.S. PATENT DOCUMENTS

2010/0207042 A1\* 8/2010 Harada ................ A61N 5/1049
250/492.3
2012/0061582 A1 3/2012 Iwata

FOREIGN PATENT DOCUMENTS

| CN | 101903063 A | 12/2010 |
| CN | 102512764 | 6/2012 |

(Continued)

OTHER PUBLICATIONS

International Search Report for Application No. PCT/CN2015/089550, dated Nov. 25, 2015, English translation.
(Continued)

*Primary Examiner* — Nicole M Ippolito
(74) *Attorney, Agent, or Firm* — Squire Patton Boggs (US) LLP (57) ABSTRACT

Provided are a respiratory guiding device (100) and method used in respiratory gated ion beam irradiation, the respiratory guiding device (100) comprising: a respiratory signal detecting unit (101), for measuring a respiratory motion trajectory curve during free breathing and deep breathing, and a real-time respiratory motion position signal in the case of guided respiration; a respiratory signal processing unit (102), for modeling free breathing and deep breathing
(Continued)

according to an average respiratory cycle and an average respiratory amplitude calculated on the basis of the respiratory motion trajectory curve and setting a preset breath-hold time at the tail end of a function curve of a free breathing model and a deep breathing model to establish a respiratory guiding curve; a control unit (103), for adjusting the magnetic excitation cycle of a synchrotron according to the respiratory cycle represented by the respiratory guiding curve during free breathing or deep breathing, thus synchronizing the magnetic excitation cycle of the synchrotron with the respiratory cycle. The device and method effectively reduce residual motion in a target region within a guided respiration window, and improve irradiation efficiency and precision of an ion beam.

16 Claims, 10 Drawing Sheets

(52) U.S. Cl.
CPC ............... *A61N 2005/1074* (2013.01); *A61N 2005/1087* (2013.01)

(58) Field of Classification Search
USPC .............. 250/396 R, 397, 492.1, 492.3
See application file for complete search history.

(56) References Cited

FOREIGN PATENT DOCUMENTS

| CN | 104274914 A | 1/2015 |
|---|---|---|
| CN | 104274914 A | 1/2015 |
| JP | 2005074156 A | 3/2005 |
| WO | WO 2012/118228 | 9/2012 |

OTHER PUBLICATIONS

Pengbo He et al., "Respiratory motion management using audio-visual biofeedback for respiratory-gated radiotherapy of synchrotron-based pulsed heavy-ion beam delivery," Med. Phys. 41 (11), Nov. 2014, pp. 111708-1-111708-11.

Extended European Search Report dated Jun. 28, 2017 for Application No. 15845487.6, 7 pages.

He, Pengbo, et al. "Effectiveness of respiratory-gated radiotherapy with audio-visual biofeedback for synchrotron-based scanned heavy-ion beam delivery," 2016 Institute of Physics and Engineering in Medicine, Phys. Med. Biol. 61, Nov. 15, 2016, pp. 8541-8552.

He, Pengbo, et al. "Respiratory Motion management using audio-visual biofeedback for respiratory-gated radiotherapy of synchrotron-based pulsed heavy-ion beam delivery," Med. Phys. 41 (11), Oct. 14, 2014, pp. 111708-1 through 111708-11.

* cited by examiner

RESPIRATORY GUIDANCE DEVICE AND METHOD APPLIED IN RESPIRATORY-GATED ION BEAM IRRADIATION

CROSS-REFERENCE TO RELATED APPLICATIONS

This application is based upon and claims priority to Chinese Patent Application No. 201410498032.9, filed Sep. 25, 2014, the entire contents of which are incorporated herein by reference.

TECHNICAL FIELD

The present disclosure relates to the field of respiratory-induced target motion compensation methods in respiratory-gated irradiation technologies using synchrotron-based pulsed ion beams to perform a conformal or intensity-modulated radiation therapy (IMRT), and more particularly, to a respiratory guidance device and method applied in a respiratory-gated irradiation using ion beams.

BACKGROUND

Compared with conventional photon (X- and γ-rays) radiotherapy, a main advantage of ion beam radiotherapy is that doses can be precisely positioned in a Bragg peak, and thus tumor cells can be efficiently killed while protecting normal tissues. Furthermore, heavy ions such as carbon ions also have characteristics such as high relative biological effectiveness (RBE) and small lateral scattering. For treatment of target volumes having relatively fixed positions and shapes, for example, head and neck tumors, an irradiation with sufficiently high accuracy can be ensured due to right positioning and immobilization for patients before the irradiation. However, tumors located in the thoracic and abdominal regions, including lung cancer, liver cancer, prostate cancer, and the like, are moved along with respiratory motions of the patients. In a therapy course, interplays between target motion and dynamic beam delivery can cause serious distortion of dose distributions, thus resulting in cold and hot spots of local doses in the target volume and limiting the normal tissue sparing potential of ion beam radiotherapy. In order to take full advantage of the ion beam therapies, and further improve the efficacy of the ion beam therapies and reduce radiation injury to the healthy tissues, it is quite necessary to carry out some research aiming at moving target irradiation techniques in the ion beam therapies, which is also the important development direction and trend in the research area of the ion beam therapies in the word.

Existing respiratory gating and breath-hold techniques have been widely used in clinical treatment to reduce or eliminate the unfavorable impact of the target motion. Recently, a new respiratory motion compensation method, in which conventional respiratory gating and breath-hold (BH) techniques and a personalized audio-visual biofeedback system are combined, was proposed by Park et al. (Y. K. Park, et al. Quasi-breath-hold technique using personalized audio-visual biofeedback for respiratory motion management in radiotherapy. Medical Physics. 2011, 38: 3114-3124). In this technique, subjects repeat physiological actions of respiratory breath-hold under the guidance of the audio-visual biofeedback system, so that respiratory frequencies and amplitudes of the subjects can become uniform, and then the target residual motions within the gating windows can be effectively reduced. Furthermore, compared with simple respiratory breath-hold techniques, this technique can reduce the complexity of doctor-patient cooperation during the treatment course. However, application objects of this technique are based on the conventional photon radiotherapy under a continuous beam delivery mode provided by a linear accelerator.

At present, there are two types of accelerator system in the ion beam radiotherapy, i.e. cyclotron and synchrotron. Cyclotron provides a continuous beam delivery mode similar to the linear accelerator, and thus it is relatively simple for optimizing respiratory-gated irradiation parameters, the target motion compensation method proposed by Park et al. can be directly translated to this setting. For ion beam acceleration systems on the basis of synchrotron, pulsed ion beams are provided, and the duration of magnet excitation cycles thereof is close to human's respiratory cycles. Usually the synchrotron uses a slow beam extraction mode, and the beams can be extracted only in a partial time of the magnet excitation cycles. An entire magnet excitation cycle includes an acceleration stage, a flat-top stage (beam extraction) and a deceleration stage. In a gated irradiation, the beams can be extracted only in a period of time that the gated-on state coincides with the flat-top stage. Thus, the premise of implementing an efficient respiratory-gated irradiation relies on the optimization of the synchronization between the magnet excitation cycle and each patient's respiratory cycle. A slight difference between the above two can result in decreased efficiency of the respiratory-gated irradiation.

Tsunashima et al. have investigated the efficiency of respiratory-gated irradiation using protons on the basis of a pulsed synchrotron (Y. Tsunashima, et al. Efficiency of respiratory-gated delivery of synchrotron-based pulsed proton irradiation. Physics in Medicine and Biology. 2008, 53: 1947-1959). In their work, a realistic simulation of the interaction of various accelerator operation parameters and patient respiratory parameters was conducted to determine optimal parameter settings, so as to improve the efficiency of the respiratory-gated proton beam irradiation. They found that the average beam delivery time was tripled by using a fixed magnet excitation cycle pattern, and the treatment time was only doubled by using a variable magnet excitation cycle pattern. In another study, they also found that the variable magnet excitation cycle method can improve the accuracy of the irradiation at the same time (Y. Tsunashima, et al. The precision of respiratory-gated delivery of synchrotron-based pulsed beam proton therapy. Physics in Medicine and Biology. 2010, 55: 7633-7647). Although this method can effectively improve the efficacy of the therapy, an implementation of a treatment plan often needs a series of pulsed beams, and each of the magnet excitation cycles must be set prior to the start of delivery for each beam, and the cycle of the next respiration of the patient needs to be predicted after the last beam spill but before the start of irradiation with the next spill. Although the method improves respiratory efficiency with respect to the fixed magnet excitation cycle mode, the complex operation process can easily cause errors, and thus the entire irradiation time is still doubled.

SUMMARY

Aiming at problems such as tedious processes, low efficiency and poor accuracy in related arts when moving targets are irradiated using synchrotron-based pulsed ion beam, an object of the present disclosure is to provide a respiratory guidance device and method applied in respiratory-gated irradiation techniques using ion beams.

In order to realize the above object, a respiratory guidance device applied in a respiratory-gated irradiation using ion beams provided by the present disclosure includes:

a respiratory signal detection unit configured to measure respiratory motion trajectory curves during free breathing and deep breathing;

a respiratory signal processing unit configured to establish a free breathing model and a deep breathing model according to average respiratory periods and average respiratory amplitudes calculated on the basis of the respiratory motion trajectory curves, and establish respiratory guidance curves by setting preset breath-hold time at the ends of function curves of the free breathing model and the deep breathing model; and a control unit configured to adjust a magnet excitation cycle of a synchrotron according to a respiratory cycle reflected by one of the respiratory guidance curves during the free breathing or the deep breathing, so that the magnet excitation cycle of the synchrotron is synchronized with the respiratory cycle.

Further, the respiratory signal processing unit includes:

a receiving part configured to receive the respiratory motion trajectory curves;

a calculation part configured to calculate the average respiratory periods and the average respiratory amplitudes according to the received respiratory motion trajectory curves; and a modeling part configured to establish the respiratory guidance curves according to the average respiratory periods, the average respiratory amplitudes and the preset breath-hold time.

Further, the modeling part includes:

a first modeling subunit configured to, according to the average respiratory amplitudes and the average respiratory periods, establish a free breathing model or a deep breathing model on the basis of the function curves; and a second modeling subunit configured to establish the respiratory guidance curves according to the free breathing model or the deep breathing model and the preset breath-hold time.

Further, if one of the average respiratory periods is greater than or equal to a predetermined time, the second modeling subunit is configured to set one function curve of the free breathing model or the deep breathing model between two successive flat-top stages of the magnet excitation cycle of the synchrotron, and set the preset breath-hold time at the end of the function curve.

Further, if one of the average respiratory periods is less than a predetermined time, the second modeling subunit is configured to set two function curves of the free breathing model or the deep breathing model between two successive flat-top stages of the magnet excitation cycle of the synchrotron, and set the preset breath-hold time at the ends of the two function curves.

Further, the respiratory guidance device further includes:

an irradiation unit configured to, if the magnet excitation cycle of the synchrotron is synchronized with the respiratory cycle reflected by one of the respiratory guidance curves, perform an ion beam irradiation; and a display unit configured to display the respiratory motion trajectory curves, the respiratory guidance curves, respiratory gating signals and magnet excitation signals of the synchrotron.

Further, the irradiation duration of the irradiation unit is related to a breath-hold duration reflected by one of the respiratory guidance curves.

A respiratory guidance method applied in a respiratory-gated irradiation using ion beams provided by the present disclosure includes the following steps:

measuring respiratory motion trajectory curves during free breathing and deep breathing;

calculating average respiratory periods and average respiratory amplitudes according to the respiratory motion trajectory curves, so as to establish respiratory guidance curves; and adjusting a magnet excitation cycle of a synchrotron according to a respiratory cycle reflected by one of the respiratory guidance curves during the free breathing or the deep breathing, so that the magnet excitation cycle of the synchrotron is synchronized with the respiratory cycle.

Further, calculating the average respiratory periods and the average respiratory amplitudes according to the respiratory motion trajectory curves, so as to establish respiratory guidance curves, includes:

according to the average respiratory amplitudes and the average respiratory periods, establishing a free breathing model or a deep breathing model on the basis of function curves; and establishing the respiratory guidance curves according to the free breathing model or the deep breathing model and preset breath-hold time.

Further, the preset breath-hold time is related to the flat-top time of the magnet excitation cycle of the synchrotron.

Further, if the average respiratory periods are greater than or equal to a predetermined time, setting one function curve of the free breathing model or the deep breathing model between two successive flat-top stages of the magnet excitation cycle of the synchrotron, and setting the preset breath-hold time at the end of the function curve.

Further, if the average respiratory periods are less than a predetermined time, setting two function curves of the free breathing model or the deep breathing model between two successive flat-top stages of the magnet excitation cycle of the synchrotron, and setting the preset breath-hold time at the ends of the two function curves.

Further, the respiratory guidance method further includes:

if the respiratory cycle reflected by one of the respiratory guidance curves is synchronized with the magnet excitation cycle of the synchrotron, performing an ion beam irradiation.

Advantageous effects of the present disclosure are as follows: the magnet excitation cycle of the synchrotron can be adjusted according to the respiratory cycle reflected by the respiratory guidance curve during the free breathing or the deep breathing, so that the magnet excitation cycle of the synchrotron is synchronized with the respiratory cycle. In addition, the target residual motions within the gating windows can be effectively reduced by combining breath-hold techniques, and thus the efficiency and accuracy of the ion beam irradiation can be improved.

BRIEF DESCRIPTION OF THE DRAWINGS

As shown in FIGS. 3 and 5, "1" represents a respiratory signal detection device, "2" represents a display, "3" represents a loudspeaker, "4" represents a computer, "5" represents a gating threshold, "6" represents a real-time respiratory motion curve, "7" represents a respiratory guidance curve, "8" represents gating signals, and "9" represents real-time beam delivery signals.

DETAILED DESCRIPTION

Preferred embodiments of the present disclosure will be described in further detail with reference to drawings.

Figure 1:
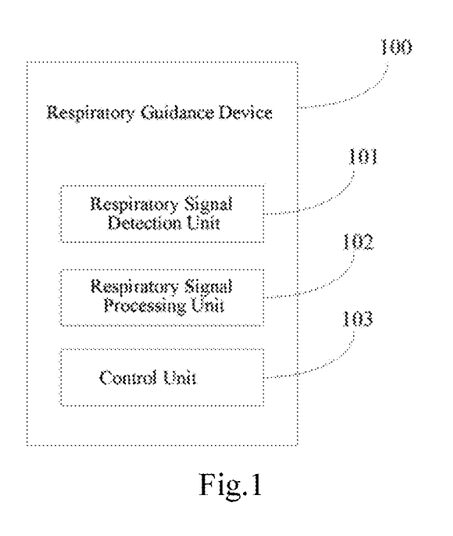
FIG. 1 is a schematic diagram of a respiratory guidance device according to an embodiment of the present disclosure.

As shown in FIG. 1, a respiratory guidance device 100 applied in a respiratory-gated irradiation using ion beams according to an embodiment of the present disclosure includes: a respiratory signal detection unit 101, a respiratory signal processing unit 102 and a control unit 103.

The respiratory signal detection unit 101 is configured to measure respiratory motion trajectory curves during free breathing and deep breathing.

The respiratory signal processing unit 102 is configured to establish a free breathing model and a deep breathing model according to the average respiratory periods and average respiratory amplitudes calculated on the basis of the respiratory motion trajectory curves, and establish respiratory guidance curves by setting preset breath-hold time at the ends of function curves of the free breathing model and the deep breathing model.

The control unit 103 is configured to adjust a magnet excitation cycle of a synchrotron according to a respiratory cycle reflected by one of the respiratory guidance curves during the free breathing or the deep breathing, so that the magnet excitation cycle of the synchrotron is synchronized with the respiratory cycle. Hereinafter, operation connection relationships between various parts in the respiratory guidance device will be described with reference to FIG. 3.

In the present disclosure, the magnet excitation cycle of the synchrotron can be adjusted according to the respiratory cycle reflected by the respiratory guidance curve having a short breath-hold at the end expiration phase during the free breathing or the deep breathing, so that the magnet excitation cycle of the synchrotron is synchronized with the respiratory cycle. In addition, subjects repeat physiological actions of the respiratory breath-hold under the guidance of the audio-visual biofeedback system, so that respiratory breath-hold phases coincide with the beam extraction stages in the magnet excitation cycle of the synchrotron, thus the efficiency of the respiratory-gated irradiation can be improved effectively while reducing target residual motions within the gating windows, and thereby the efficiency and accuracy of the ion beam irradiation can be improved.

In one embodiment, the respiratory guidance device further includes: an irradiation unit and a display unit.

The irradiation unit is configured to, if the magnet excitation cycle of the synchrotron is synchronized with the respiratory cycle reflected by one of the respiratory guidance curves, perform an ion beam irradiation.

The display unit is configured to display the respiratory motion trajectory curves, the respiratory guidance curves, respiratory gating signals and magnet excitation signals of the synchrotron.

In one embodiment, the respiratory signal processing unit includes: a receiving part, a calculation part and a modeling part.

The receiving part is configured to receive the respiratory motion trajectory curves.

The calculation part is configured to calculate the average respiratory periods and the average respiratory amplitudes according to the received respiratory motion trajectory curves.

The modeling part is configured to establish the respiratory guidance curves according to the average respiratory periods, the average respiratory amplitudes and the preset breath-hold time.

In one embodiment, the modeling part includes: a first modeling subunit and a second modeling subunit.

The first modeling subunit is configured to, according to the average respiratory amplitudes and the average respiratory periods, establish a free breathing model or a deep breathing model on the basis of the function curves.

The second modeling subunit is configured to establish the respiratory guidance curves according to the free breathing model or the deep breathing model and the preset breath-hold time. Specific steps for establishing the respiratory guidance curves can refer to the following descriptions and FIG. 6.

Figure 3:
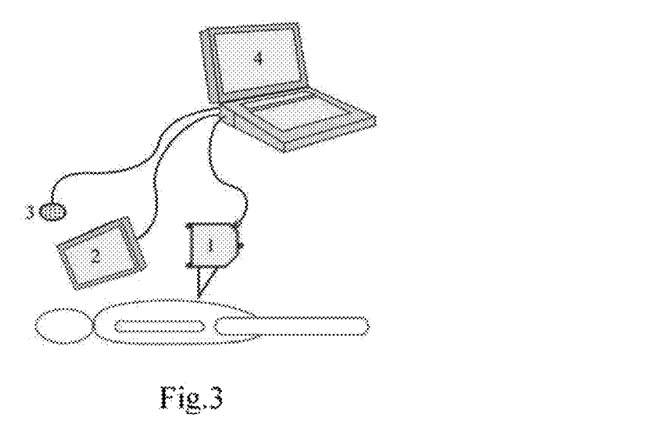
FIG. 3 is a structural principle diagram of the respiratory guidance device in FIG. 1.

As shown in FIG. 3, in above embodiments of the present disclosure, characteristics of the respiratory guidance device applied in the respiratory-gated irradiation using ion beams are that the respiratory guidance device includes: a respiratory signal detection device 1 recording respiratory motion trajectories in real time, the respiratory signal detection device 1 is connected to a computer 4, and visual feedback information thereof is displayed on a display 2 through the computer 4; a loudspeaker 3 performing audio feedback to assist visual feedback is mounted in an irradiation room, and is connected to the computer 4 with software of a control system installed, so as to process above measured signals and control the synchronization between the magnet excitation cycle of the synchrotron and the respiratory cycle.

In above embodiments of the present disclosure, an audio-visual biofeedback system is made of the respiratory signal detection device, the display, the loudspeaker, the computer and the control system. In the audio-visual biofeedback system, the respiratory signal detection device is configured to detect position information of markers placed on abdomens of the subjects, so as to reflect the respiratory motion trajectories of the subjects. Sampling frequencies of respiratory signals of the respiratory signal detection device have a range of 10 to 50 Hz. The display is configured to display the real-time respiratory motion trajectories and personalized respiratory guidance curves of the subjects, and both of which are arranged in front of the subjects, so as to ensure that the subjects can see his/her own real-time respiratory motion trajectories and personalized respiratory guidance curves.

Figure 2:
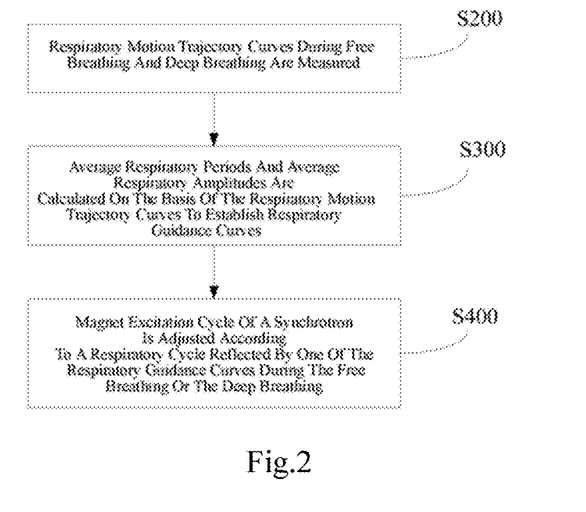
FIG. 2 is a schematic flow chart of a respiratory guidance method according to an embodiment of the present disclosure.

As shown in FIG. 2, a respiratory guidance method applied in a respiratory-gated irradiation using ion beams according to an embodiment of the present disclosure includes the following steps.

In S200, respiratory motion trajectory curves during free breathing and deep breathing are measured.

In S300, average respiratory periods and average respiratory amplitudes are calculated according to the respiratory motion trajectory curves, so as to establish respiratory guidance curves.

In S400, a magnet excitation cycle of a synchrotron is adjusted according to a respiratory cycle reflected by one of the respiratory guidance curves during the free breathing or the deep breathing, so that the magnet excitation cycle of the synchrotron is synchronized with the respiratory cycle. Hereinafter, each step in the respiratory guidance method will be described with reference to FIGS. 4 and 6.

Figure 4:
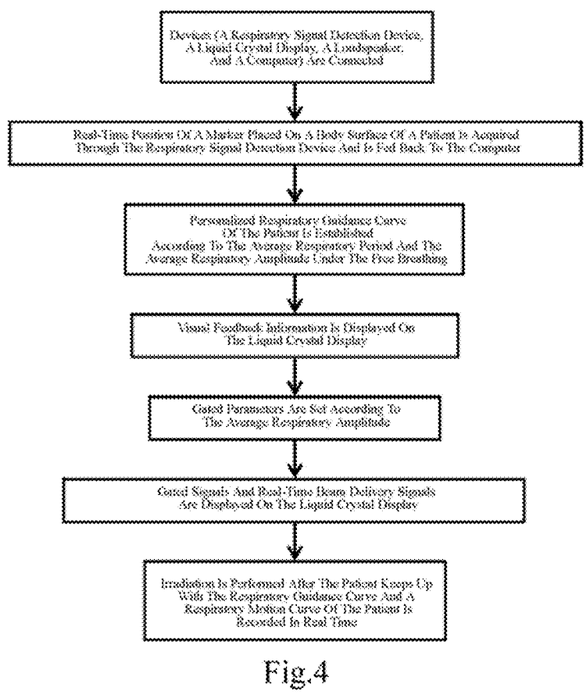
FIG. 4 is a specific flow chart of the respiratory guidance method in FIG. 2.
Figure 5:
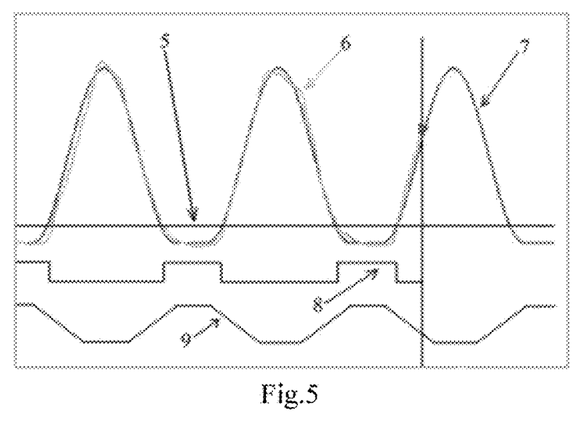
FIG. 5 is visual feedback information displayed on an interface of a software of the present disclosure.

As shown in FIG. 4, real-time position information of the markers placed on body surfaces of the subjects are acquired by the control system through the respiratory signal detection device 1; average respiratory periods and average respiratory amplitudes are calculated by measuring respiratory motion trajectory curves of the subjects during the free breathing and deep breathing; and personalized respiratory guidance curves are established according to the average respiratory periods and the average respiratory amplitudes. The method for establishing the personalized respiratory guidance curves is shown in FIG. 6; a respiratory guidance curve 7 for visual feedback and real-time respiratory motion curves 6 of the subjects are displayed on the display 2, as shown in FIG. 5; a respiratory gating threshold 5 is set according to the average respiratory amplitudes of the subjects; gating signals 8 and real-time beam delivery signals 9 are displayed on the display 2, as shown in FIG. 5; and the irradiation is performed after the real-time respiratory motion curves of the subjects keep up with the respiratory guidance curve 7 while recording the respiratory motion curves of the subjects during the irradiation.

Figure 6:
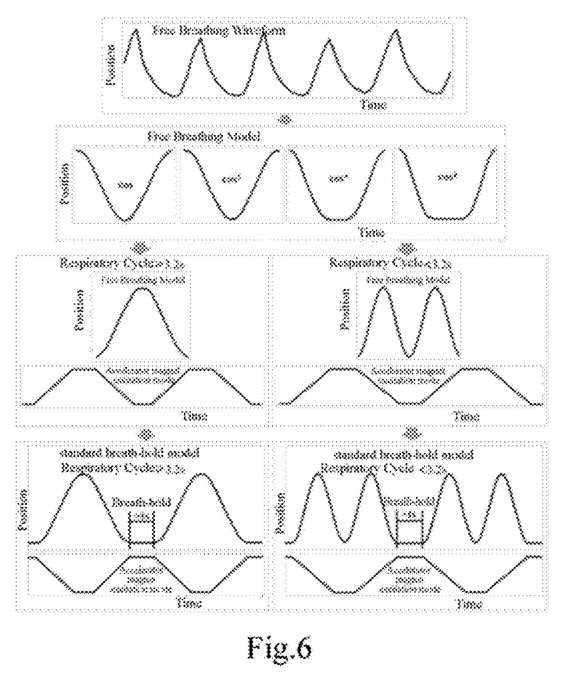
FIG. 6 is a flow chart for establishing a personalized respiratory guidance curve of the present disclosure.

As shown in FIG. 6, the respiratory guidance method applied in a respiratory-gated irradiation using ion beams includes the following steps.

Step (1), operating parameters of the synchrotron are set. In order to synchronize the respiratory cycles of the subjects with the magnet excitation cycle of the synchrotron, parameters such as the magnet excitation cycle of the synchrotron and beam extraction time need to be set by an accelerator control system, so as to divide the entire magnet excitation cycle into three stages, i.e. an acceleration period, a flat-top time and a deceleration period. The acceleration period and the deceleration period are fixed values having a range of 1.0 to 3.0 s, respectively, and do not change with beam energy. The flat-top time is an adjustable value having an adjustable range of 0.0 to 10.0 s. The magnet excitation cycle needs to be set before the next pulse starts, and once it is set, the magnet excitation cycle cannot be changed before the pulse ends.

Here, the description will be made with reference to operating parameters of a heavy ion medical machine (HIMM). The HIMM facility uses a synchrotron as a main accelerator, and uses a cyclotron as an injector. The acceleration period and the deceleration period of the synchrotron are fixed to 1.6 s, respectively, the flat-top time has an adjustable range of 0.0 to 10.0 s, and thus the magnet excitation cycle has an adjustable range of 3.2 to 13.2 s.

Step (2), the personalized respiratory guidance curves are established. Firstly, four to five respiratory cycle motion trajectories of the subjects during free breathing are measured and recorded in time sequence, and a free breathing (FB) model on the basis of a $\cos^2$, $\cos^4$, or $\cos^6$ function curve can be established according to the average respiratory amplitude and the average respiratory period. Secondly, a synchronization model between a respiratory mode and a magnet excitation mode of the synchrotron is established. For the synchrotron of the HIMM facility, if the average respiratory period of the subject is greater than or equal to 3.2 s, one FB model is set between two successive flat-top states of the cycle of the synchrotron; otherwise, two successive FB models are set, because the time interval between two successive flat-top states is at least 3.2 s (the deceleration time is 1.6 s, and the acceleration time is 1.6 s), and the respiratory cycle of an ordinary person is generally greater than 1.6 s, the highest irradiation efficiency can be obtained through such settings. Furthermore, because the FB model is established on the basis of the average respiratory amplitude and the average respiratory period of the subject during the free breathing, the burden of the subject can be reduced to some extent. Finally, a breath-hold (BH) signal having a duration of 1.0 s is added to the end of the curve of the FB model, and then this procedure is continuously repeated, in this way, a complete standard breath-hold (stBH) model is established. Meanwhile, the magnet excitation mode of the synchrotron can also be determined, and if the average respiratory period of the subject is greater than or equal to 3.2 s, the magnet excitation cycle equals to a duration of the respiratory cycle plus a flat-top time of 1.0 s; otherwise, one magnet excitation cycle equals to durations of two respiratory cycles plus a flat-top time of 1.0 s. Using the same method, a standard short deep breath-hold (stSDBH) model is established.

Figure 7:
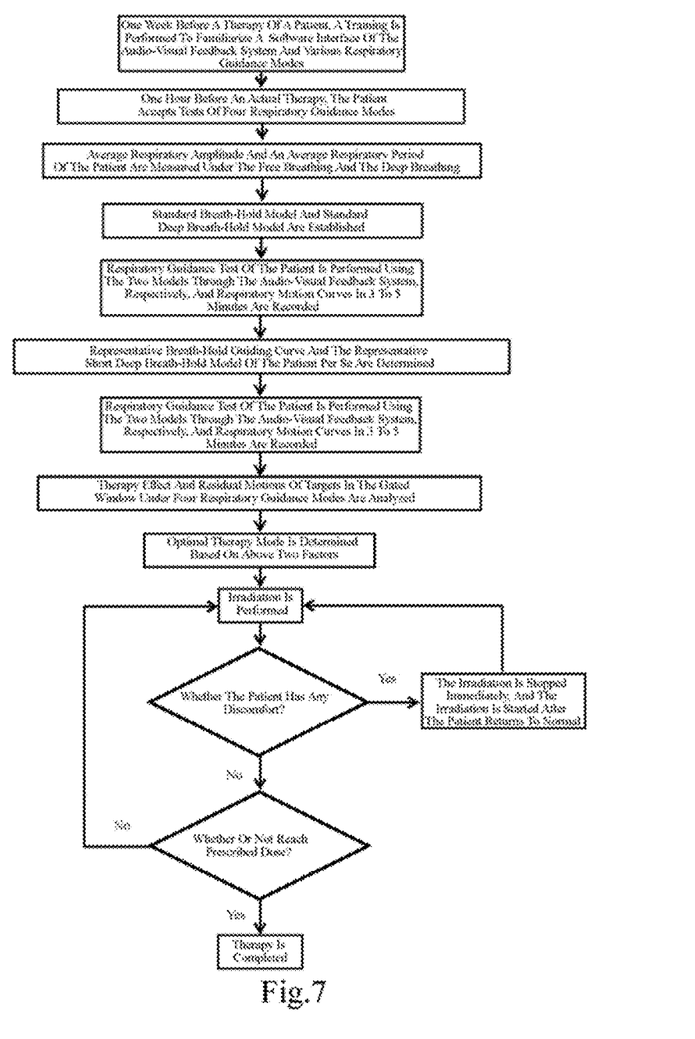
FIG. 7 is a flow chart of a respiratory guidance irradiation of the present disclosure.

Step (3), a respiratory guidance irradiation is performed. As shown in FIG. 7, one week before the irradiation, the subject needs to receive a training which includes familiarity with a software interface of the audio-visual biofeedback system, and familiarity with various respiratory guidance modes such as stBH, representative breath-hold (reBH), stSDBH, representative short deep breath-hold (reSDBH). One hour before an actual irradiation, the subject needs to receive tests of four respiratory guidance modes, so as to determine that which mode can be used to obtain the highest irradiation efficiency while minimizing residual motions of the target volumes in the respiratory gating window.

In step (1), the synchrotron uses a slow extraction way to extract beams during the flat-top phase. The slow extraction time is an adjustable value, and if the slow extraction time is less than the flat-top time, all ions have been extracted before normal completion of the flat-top phase, at this time, a deceleration phase starts. Afterwards, the synchrotron is in a non-magnetic excitation state until the magnet excitation cycle ends, and then enters the next magnet excitation cycle. Characteristics of the synchrotron enable the magnet excitation cycle of the synchrotron to be set as the respiratory cycle of the subject conveniently and flexibly, and enable the personalized respiratory guidance curve of the subject to be established, so as to instruct the subject to repeat the same respiratory mode, and thus improving the irradiation efficiency.

In step (2), the free breathing model may not be able to reflect a real respiratory mode of the subject, thereby, real respiratory data of the subject in one to two cycles can be recorded as a reBH guidance curve of the subject during implementation of a standard breath-hold mode guidance, and it is easier for the subject to accept respiratory guidance by using the reBH guidance curve of the subject. Using the same method, a reSDBH model of the subject is established.

In step (2), in the case that a free breathing cycle of some subjects is less than 3.2 s and a deep breathing cycle is greater than 3.2 s, using the short deep breath-hold model to perform the respiratory guidance can further improve the irradiation efficiency, and using which kind of respiratory guidance models needs to be selected according to actual respiration state of the subject.

In step (3), the processes of the respiratory guidance irradiation include the following steps.

In a first step, average respiratory amplitudes and average respiratory periods of the subjects during the free breathing and the deep breathing are measured respectively, and a stBH model and a stSDBH model are established based on the average respiratory amplitudes and the average respiratory periods.

In a second step, respiratory guidance tests of the subjects are performed using the two models through the audio-visual biofeedback system, and respiratory motion trajectories in 3 to 5 minutes are recorded.

In a third step, a reBH guidance curve and the reSDBH model of the subjects are determined respectively during a standard respiratory guidance, and respiratory motion trajectories in 3 to 5 minutes under the two guidance modes are recorded again.

In a fourth step, the irradiation efficiency and target residual motions within the gating windows under four respiratory guidance modes are analyzed, and an optimal irradiation mode is determined based on above two factors, so that the effect of the therapy can be maximized.

In step (3), during the respiratory guidance irradiation, an ion beam irradiation is performed according to the selected optimal irradiation mode. If the subjects have any discomfort during the irradiation, the ion beam irradiation needs to be stopped immediately. After the subjects return to a normal state, the respiratory guidance mode is re-established, and unfinished irradiation is continued to be performed.

Specific experimental processes of the respiratory guidance device and method applied in the respiratory-gated irradiation using ion beams are as follows.

A respiratory guidance test is performed on fifteen volunteers using an audio-visual biofeedback system independently developed at the Institute of Modern Physics, Chinese Academy of Sciences, and the experimental settings are shown in FIG. 3. The fifteen volunteers include three medical physicists, three graduate students and nine general publics, and have an age range of 23 to 43 years old, as well as a weight range of 53 to 95 kg. A software for controlling the audio-visual biofeedback system is developed on Matlab (Version 7.10). Beam pulse signals simulate actual magnet excitation modes of the HIMM facility, the respiratory motion signal detection device is a laser displacement sensor (ILD1700, MICRO-EPSILON®, Germany) having an effective detection range of 200 to 950 mm and the measurement accuracy of 0.5 mm, and the display is an AOC-LM720 LCD (Liquid Crystal Display) display. One week before the simulation experiments start, the fifteen volunteers underwent a respiratory guidance training to familiarize the entire process and each respiratory guidance mode. An actual simulation test can be performed by the following five steps. In a first step, the volunteers are asked for continuous free breathing for five minutes without any guidance, and respiratory motion trajectories during this process are recorded to analyze the efficiency using the respiratory-gated irradiation under conventional free breathing modes, and are used as the control data of next respiratory guidance experiment. In a second step, during the free breathing and the deep breathing, average respiratory amplitudes and average respiratory periods of the volunteers are measured respectively, and a stBH model and a stSDBH model are established based on the average respiratory amplitude and the average respiratory period. In a third step, respiratory guidance tests of the volunteers are performed using the two models through the audio-visual biofeedback system, and respiratory motion curves in 5 minutes are recorded to prepare for subsequent analysis of the effective irradiation dose rate and target residual motions in respiratory gating windows with different sizes. In a fourth step, a reBH guidance curve and the reSDBH model of the volunteers are determined respectively during a standard respiratory guidance, and respiratory motion curves in 5 minutes under the two guidance modes are recorded again for subsequent control analysis. In a fifth step, after the above five respiratory modes are completed, the effective irradiation dose rate and the target residual motions in a range of 10% to 50% gating window under each mode are analyzed. During these tests, no volunteer appears discomfort.

Figure 8:
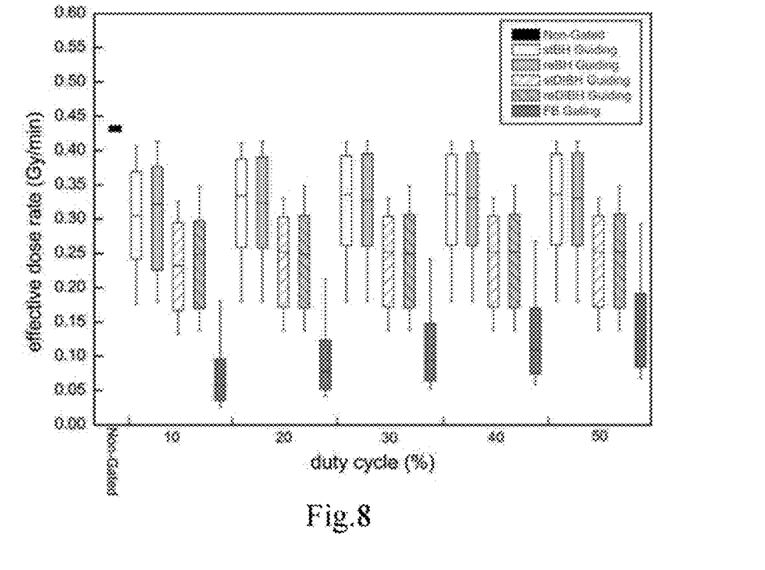
FIG. 8 is a distribution diagram of effective irradiation dose rates during experiments of the present disclosure.

FIG. 8 shows distributions of effective irradiation dose rates under situations such as non-gated, gating under the free breathing, and four respiratory guidance modes (stBH, reBH, stSDBH, reSDBH). In FIG. 8, error bars represent a maximum value and a minimum value, rectangles represent a standard deviation, and middle lines represent a mid-value. It can be seen that for the non-gated situation, the dose rate is 0.432 Gy/min; and for the free breathing model, the dose rate within 50% to 10% gating window has decreased by 2.13 to 5.56 times, respectively. Compared with a non-gated mode, the dose rate has decreased by 0.31-0.41, 0.31-0.43, 0.81-0.87 and 0.81-0.85 times under four respiratory guidance situations, respectively. This means that using the respiratory guidance method, the irradiation efficiency of respiratory-gated irradiation for synchrotron-based pulsed ion beam can be improved.

Figure 9:
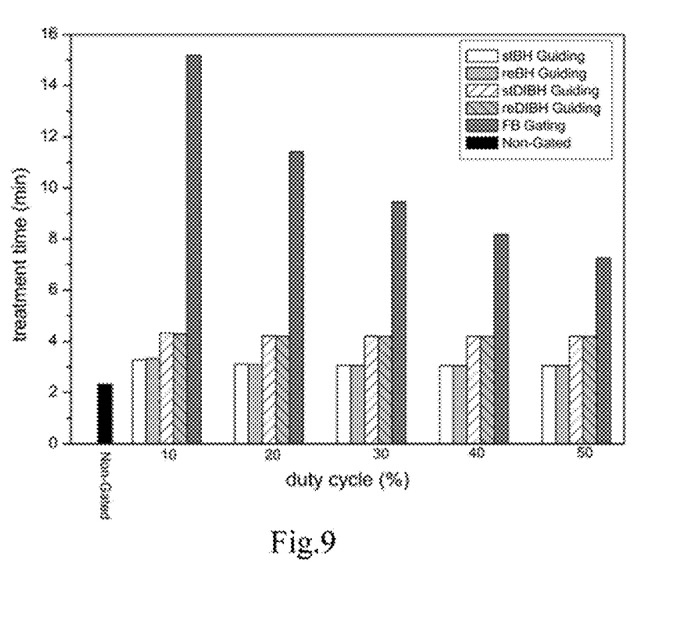
FIG. 9 a schematic diagram of irradiation time for irradiating a preset dose of 1 Gy during experiments of the present disclosure.
Figure 10:
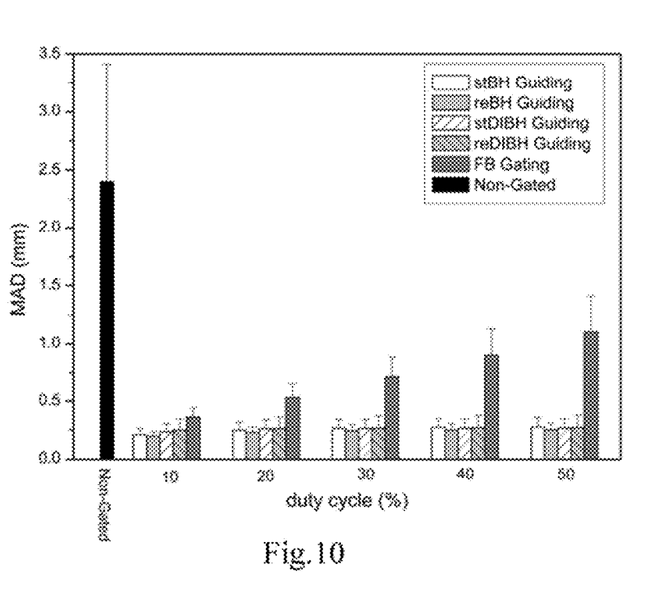
FIG. 10 is a distribution diagram of target residual motions within the gating windows during experiments of the present disclosure.

FIG. 9 shows irradiation time for irradiating a preset dose of 1 Gy. It can be seen from FIG. 9, the irradiation time is obviously reduced using the respiratory guidance method. FIG. 10 shows target residual motions under situations such as non-gated, gating under the free breathing, and four respiratory guidance modes (stBH, reBH, stSDBH, reSDBH). For the non-gated situation, the value of mean absolute deviation (MAD) is 2.40±1.01 mm. For the gating under the free breathing, values of the MADs have decreased by 1.18 to 5.67 times, and for the respiratory guidance situation, values of the MADs have decreased by nearly 10 times. This means that the accuracy of the irradiation can be greatly improved using the respiratory guidance method.

Compared with the effect of the respiratory-gated irradiation under conventional free breathing models, the respiratory guidance not only improves the irradiation efficiency, but also reduces the target residual motions within the gating windows, and thus the therapy efficacy of ion beam irradiation can be greatly improved. In addition, since the free breathing model is established on the basis of the average respiratory amplitudes and the average respiratory periods of the subjects during the free breathing, the burden of the subjects can be reduced to some extent. In view of above, it is proved that the present method is feasible.

The above embodiments are only the preferred embodiments of the present disclosure, and are not intended to limit the present disclosure. Various modifications, equivalent substitutions and adaptations within the spirit and principle of the present disclosure should be included in the protection scope of the present disclosure.

What is claimed is:

1. A respiratory guidance device applied in a respiratory-gated irradiation using ion beams, comprising:
    a respiratory signal detection unit configured to measure respiratory motion trajectory curves during free breathing and deep breathing;
    a respiratory signal processing unit configured to establish a free breathing model and a deep breathing model according to average respiratory periods and average respiratory amplitudes calculated on the basis of the respiratory motion trajectory curves, and establish respiratory guidance curves by setting preset breath-hold time at the ends of function curves of the free breathing model and the deep breathing model; and
    a control unit configured to adjust a magnet excitation cycle of a synchrotron according to a respiratory cycle reflected by one of the respiratory guidance curves during the free breathing or the deep breathing, so that the magnet excitation cycle of the synchrotron is synchronized with the respiratory cycle;
    wherein the respiratory signal processing unit comprises:
    a receiving part configured to receive the respiratory motion trajectory curves;
    a calculation part configured to calculate the average respiratory periods and the average respiratory amplitudes according to the received respiratory motion trajectory curves; and
    a modeling part configured to establish the respiratory guidance curves according to the average respiratory periods, the average respiratory amplitudes and the preset breath-hold time.

2. The respiratory guidance device according to claim 1, wherein the modeling part comprises:
    a first modeling subunit configured to, according to the average respiratory amplitudes and the average respiratory periods, establish a free breathing model or a deep breathing model on the basis of the function curves; and
    a second modeling subunit configured to establish the respiratory guidance curves according to the free breathing model or the deep breathing model and the preset breath-hold time.

3. The respiratory guidance device according to claim 2, wherein, if the average respiratory periods are greater than or equal to a predetermined time, the second modeling subunit is configured to set one function curve of the free breathing model or the deep breathing model between two successive flat-top stages of the magnet excitation cycle of the synchrotron, and set the preset breath-hold time at the end of the function curve.

4. The respiratory guidance device according to claim 2, wherein, if the average respiratory periods are less than a predetermined time, the second modeling subunit is configured to set two function curves of the free breathing model or the deep breathing model between two successive flat-top stages of the magnet excitation cycle of the synchrotron, and set the preset breath-hold time at the ends of the two function curves.

5. The respiratory guidance device according to claim 1, further comprising:
    an irradiation unit configured to, if the magnet excitation cycle of the synchrotron is synchronized with the respiratory cycle reflected by one of the respiratory guidance curves, perform an ion beam irradiation; and
    a display unit configured to display the respiratory motion trajectory curves, the respiratory guidance curves, respiratory gating signals and magnet excitation signals of the synchrotron.

6. The respiratory guidance device according to claim 5, wherein an irradiation duration of the irradiation unit is related to a breath-hold duration reflected by one of the respiratory guidance curves.

7. A respiratory guidance method applied in a respiratory-gated irradiation using ion beams, comprising:
    measuring respiratory motion trajectory curves during free breathing and deep breathing;
    calculating average respiratory periods and average respiratory amplitudes according to the respiratory motion trajectory curves, so as to establish respiratory guidance curves; and
    adjusting a magnet excitation cycle of a synchrotron according to a respiratory cycle reflected by one of the respiratory guidance curves during the free breathing or the deep breathing, so that the magnet excitation cycle of the synchrotron is synchronized with the respiratory cycle;
    wherein calculating the average respiratory periods and the average respiratory amplitudes according to the respiratory motion trajectory curves, so as to establish respiratory guidance curves comprises:
    according to the average respiratory amplitudes and the average respiratory periods, establishing a free breathing model or a deep breathing model on the basis of function curves; and
    establishing the respiratory guidance curves according to the free breathing model or the deep breathing model and preset breath-hold time.

8. The respiratory guidance method according to claim 7, wherein, if the average respiratory periods are greater than or equal to a predetermined time, setting one function curve of the free breathing model or the deep breathing model between two successive flat-top stages of the magnet excitation cycle of the synchrotron, and setting the preset breath-hold time at the end of the function curve.

9. The respiratory guidance method according to claim 7, wherein, if the average respiratory periods are less than a predetermined time, setting two function curves of the free breathing model or the deep breathing model between two successive flat-top stages of the magnet excitation cycle of the synchrotron, and setting the preset breath-hold time at the ends of the two function curves.

10. The respiratory guidance method according to claim 7, further comprising:
    if the respiratory cycle reflected by one of the respiratory guidance curves is synchronized with the magnet excitation cycle of the synchrotron, performing an ion beam irradiation.

11. The respiratory guidance method according to claim 7, further comprising:
    repeating physiological actions of respiratory breath-hold under the guidance of the respiratory guidance curves displayed on a display, so that respiratory breath-hold phases of subjects coincide with beam extraction stages in the magnet excitation cycle of the synchrotron.

12. A respiratory guidance device applied in a respiratory-gated irradiation using ion beams, comprising:
    a processor; and
    a memory for storing instructions executable by the processor;

wherein the processor is configured to:
measure respiratory motion trajectory curves during free breathing and deep breathing;
calculate average respiratory periods and average respiratory amplitudes according to the respiratory motion trajectory curves, so as to establish respiratory guidance curves; and
adjust a magnet excitation cycle of a synchrotron according to a respiratory cycle reflected by one of the respiratory guidance curves during the free breathing or the deep breathing, so that the magnet excitation cycle of the synchrotron is synchronized with the respiratory cycle;
wherein the processor is configured to:
according to the average respiratory amplitudes and the average respiratory periods, establish a free breathing model or a deep breathing model on the basis of function curves; and
establish the respiratory guidance curves according to the free breathing model or the deep breathing model and preset breath-hold time.

13. The respiratory guidance device according to claim 12, wherein, if the average respiratory periods are greater than or equal to a predetermined time, setting one function curve of the free breathing model or the deep breathing model between two successive flat-top stages of the magnet excitation cycle of the synchrotron, and setting the preset breath-hold time at the end of the function curve.

14. The respiratory guidance device according to claim 12, wherein, if the average respiratory periods are less than a predetermined time, setting two function curves of the free breathing model or the deep breathing model between two successive flat-top stages of the magnet excitation cycle of the synchrotron, and setting the preset breath-hold time at the ends of the two function curves.

15. The respiratory guidance device according to claim 12, wherein the processor is configured to:
if the respiratory cycle reflected by one of the respiratory guidance curves is synchronized with the magnet excitation cycle of the synchrotron, perform an ion beam irradiation.

16. The respiratory guidance device according to claim 12, wherein the processor is configured to:
repeat physiological actions of respiratory breath-hold under the guidance of the respiratory guidance curves displayed on a display, so that respiratory breath-hold phases of subjects coincide with beam extraction stages in the magnet excitation cycle of the synchrotron.

* * * * *